(12) United States Patent
Ueda et al.

(10) Patent No.: US 9,205,247 B2
(45) Date of Patent: Dec. 8, 2015

(54) CONNECTION PORT AND DIALYSIS APPARATUS HAVING CONNECTION PORT

(71) Applicants: NIPRO CORPORATION, Osaka-shi, Osaka (JP); SHIBUYA KOGYO CO., LTD., Kanazawa-shi, Ishikawa (JP)

(72) Inventors: Mitsutaka Ueda, Osaka (JP); Toshiharu Sawada, Kanazawa (JP); Inobu Fujikawa, Kanazawa (JP)

(73) Assignees: NIPRO CORPORATION, Osaka-shi, Osaka (JP); SHIBUYA KOGYO CO., LTD., Kanazawa-shi, Ishikawa (JP)

( * ) Notice: Subject to any disclaimer, the term of this patent is extended or adjusted under 35 U.S.C. 154(b) by 0 days.

(21) Appl. No.: 14/406,005

(22) PCT Filed: Jun. 13, 2013

(86) PCT No.: PCT/JP2013/066298
§ 371 (c)(1),
(2) Date: Dec. 5, 2014

(87) PCT Pub. No.: WO2013/187459
PCT Pub. Date: Dec. 19, 2013

(65) Prior Publication Data
US 2015/0151104 A1 Jun. 4, 2015

(30) Foreign Application Priority Data

Jun. 13, 2012 (JP) .................................. 2012-133504

(51) Int. Cl.
| | |
|---|---|
| *A61M 39/16* | (2006.01) |
| *A61M 1/34* | (2006.01) |
| *A61M 1/16* | (2006.01) |
| *A61M 39/00* | (2006.01) |

(52) U.S. Cl.
CPC ............. *A61M 39/16* (2013.01); *A61M 1/1686* (2013.01); *A61M 1/342* (2013.01); *A61M 1/3424* (2014.02); *A61M 2039/0009* (2013.01); *A61M 2039/167* (2013.01)

(58) Field of Classification Search
CPC .... A61M 1/1686; A61M 1/342; A61M 39/16
USPC .......................................... 422/307; 137/238
See application file for complete search history.

(56) References Cited

U.S. PATENT DOCUMENTS 4,745,950 A   5/1988   Mathieu

FOREIGN PATENT DOCUMENTS

| JP | 61-288866 A | 12/1986 |
|---|---|---|
| JP | 03-073162 A | 3/1991 |
| JP | 10-504204 A | 4/1998 |
| JP | 10-263077 A | 10/1998 |
| JP | 3810548 B2 | 6/2006 |

OTHER PUBLICATIONS

International Search Report for PCT/JP2013/066298 (2 pgs.).

*Primary Examiner* — Sean E Conley
(74) *Attorney, Agent, or Firm* — Flynn, Thiel, Boutell & Tanis, P.C.

(57) ABSTRACT

A connection port 31 includes a cylindrical outer port 42 to which downstream piping 30*b* (discharge-side piping) is connected; an inner port 43 to which upstream piping 30*a* (supply-side piping) is connected, and which is provided in the outer port; and a lid member 44 which closes the inner port as well as the outer port. The inner port is provided so as to extend through the outer port from the outside of the outer port, and a heater H is provided on a portion of the inner port projecting outside the outer port. When the lid member is in a closed state, the inner port is heated with the heater to sterilize the portion of the inner port exposed to the outside, thus enabling the connection port to be cleaned at a higher level.

3 Claims, 2 Drawing Sheets

CONNECTION PORT AND DIALYSIS APPARATUS HAVING CONNECTION PORT

TECHNICAL FIELD

The present invention relates to a connection port and a dialysis apparatus having the connection port and, more particularly, to a connection port having a cylindrical outer port, an inner port provided in the outer port and a lid member which closes the inner port as well as the outer port and to a dialysis apparatus having the connection port.

BACKGROUND ART

Conventionally, a dialysis apparatus or the like in which a liquid is flowed is provided with a connection port to which a passage for flowing the liquid is connected. One connection port known as such a connection port has a cylindrical outer port to which a liquid-discharge-side passage is connected, an inner port to which a liquid-supply-side passage is connected and which is provided in the outer port, and a lid member which closes the inner port as well as the outer port (Patent Literature 1).

In such a connection port, when the lid member is in a closed state, the liquid from the inner port is flowed through a space formed by the lid member and the outer port and discharged from the outer port. When the lid member is in the open state, the inner port is exposed to the outside and a liquid passage can be connected to the inner port.

PRIOR ART DOCUMENT

Patent Literature

Patent Literature 1: Japanese Patent No. 3810548

SUMMARY OF INVENTION

Problem to be Solved by the Invention

As the above-described dialysis apparatus, a dialysis apparatus configured to perform on-line HDF, i.e., to supply a dialysis solution to a patient by flowing the dialysis solution from a dialysis solution circuit directly to a blood circuit, is known.

In such a dialysis apparatus, a replacement fluid passage branching off from the blood circuit is connected to the connection port provided on the dialysis solution circuit to supply the dialysis solution to a patient. It is, therefore, necessary to maintain good hygiene particularly in the connection port.

In the connection port in Patent Literature 1, however, only the inner port is cleaned at the time of cleaning of the dialysis solution passage by setting the lid member in the closed state and flowing a cleaning liquid through the space formed between the outer port and the lid member. There is a demand for a higher level of cleaning.

In consideration of this problem, an object of the present invention is to provide a connection port capable of achieving a higher level of cleaning and a dialysis apparatus having the connection port.

Means for Solving the Problems

A connection port according to the present invention includes: a cylindrical outer port to which liquid discharge-side piping is connected; an inner port to which liquid supply-side piping is connected, and which is provided in the outer port; and a lid member which closes the outer port, a liquid from the inner port being flowed through a space formed by the lid member and the outer port and discharged from the outer port when the lid member is in a closed state, the inner port being exposed to the outside when the lid member is in an open state, enabling a liquid passage to be connected to the inner port. In the connection port, the inner port is provided so as to extend through the outer port from the outside of the outer port, and a heater is provided on a portion of the inner port projecting outside the outer port. When the lid member is in the closed state, the inner port is heated with the heater to sterilize the portion of the inner port exposed to the outside.

In a connection port according to an embodiment of the present invention, the outer port is in the form of a cylinder with a closed bottom and is made of a heat-resistant resin; the inner port extends through the bottom of the outer port; a flange is formed on the portion of the inner port extending through the outer port; and a recessed portion into which the flange is fitted is formed in the bottom portion of the outer port.

A dialysis apparatus according to an embodiment of the present invention having the connection port and including: a dialyzer for performing hemodialysis; a blood circuit for flowing blood through the dialyzer; and a dialysis solution circuit for flowing a dialysis solution through the dialyzer. In the dialysis apparatus, a replacement fluid passage branching off from the blood circuit is provided; the connection port to which the replacement fluid passage can be connected is provided in the dialysis solution circuit; and the inner port is heated with the heater to sterilize a portion of the inner port connected to the replacement fluid passage.

Advantageous Effects of Invention

In the present invention, the portion of the inner port exposed to the outside can be heated and sterilized by heating the inner port with the heater, thus enabling a higher level of sterilization.

In can embodiment of the present invention, the inner port and the outer port can be reliably connected to each other by fitting the flange formed on the inner port into the recessed portion formed in the outer port.

In an embodiment of the present invention, the connection port can be subjected to a high level of sterilization before the replacement fluid passage is connected to the connection port for the purpose of performing on-line HDF, thus enabling the replacement fluid passage for supply of the dialysis solution to a patient to be connected with improved safety.

MODE FOR CARRYING OUT THE INVENTION

Figure 1:
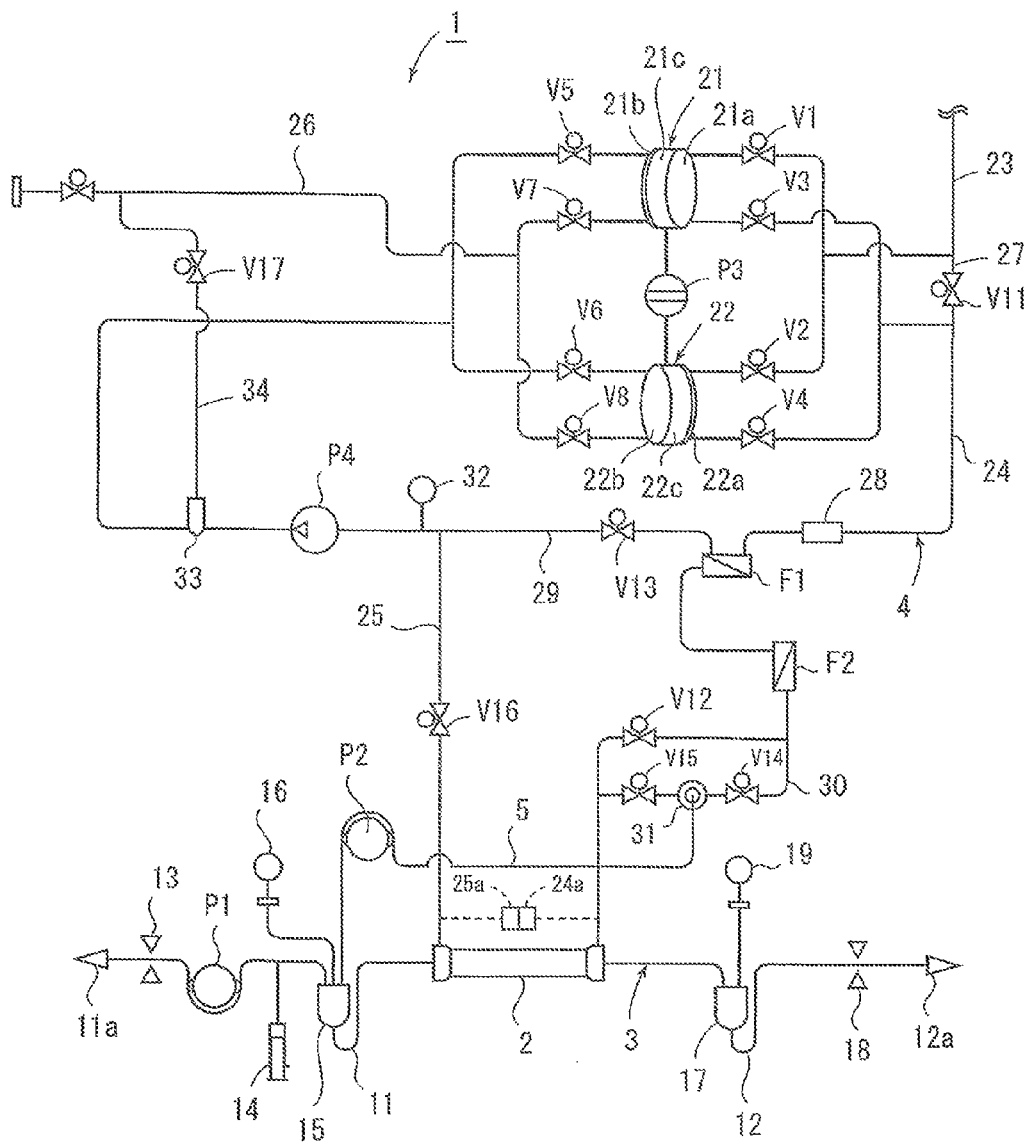
FIG. 1 is a circuit diagram of a hemodialysis apparatus according to the present embodiment.

The present invention will be described with respect to an embodiment shown in the drawings. FIG. 1 is a circuit diagram of a hemodialysis apparatus 1 for performing hemodialysis.

The hemodialysis apparatus 1 in the present embodiment is provided with a dialyzer 2 with which hemodialysis is performed, a blood circuit 3 connected to the dialyzer 2, and a dialysis solution circuit 4 connected to the dialyzer 2. The hemodialysis apparatus 1 is controlled by control means (not shown).

The hemodialysis apparatus 1 in the present embodiment is capable of performing on-line HDF by supplying a fresh dialysis solution to a patient through the blood circuit 3 and is provided with a replacement fluid passage 5 branching off from the blood circuit 3 and capable of being connected to the dialysis solution circuit 4.

The interior of the dialyzer 2 is partitioned into a blood chamber and a dialysis solution chamber by a hollow fiber membrane (not shown). Blood flows in the blood chamber in a left-to-right direction as viewed in the figure, while the dialysis solution flows in the dialysis solution chamber in a right-to-left direction as viewed in the figure.

The blood circuit 3 is provided with an artery-side passage 11 connected to an artery of a patient and to one end of the dialyzer 2, and a vein-side passage 12 connected to a vein and to the other end of the dialyzer 2. The replacement fluid passage 5 is connected so as to branch off from the artery-side passage 11.

On the artery-side passage 11, a puncturing needle 11a to be inserted in a patient, clamp means 13 for opening/closing the artery-side passage 11, a blood pump P1 for feeding blood constituted by a tube pump (peristaltic), a syringe 14 from which a blood coagulation preventive agent is supplied, a drip chamber 15 for removing air from blood and a pressure gage 16 provided on the drip chamber 15 to measure pressure are provided.

A drip chamber 17 for removing air from blood, clamp means 18 for opening/closing the vein-side passage 12 and a puncturing needle 12a to be inserted in a patient are provided on the vein-side passage 12. A pressure gage 19 is provided on the drip chamber 17.

The replacement fluid passage 5 is connected to the drip chamber 15 in the artery-side passage 11. The replacement fluid passage 5 is exchanged together with the dialyzer 2 and blood circuit 3 each time dialysis treatment is performed.

A connector (not shown), which is to be connected to a replacement fluid port 31 provided as a connection port described below, is provided on an end portion of the replacement fluid passage 5. Further, a replacement fluid pump P2 constituted by a tube pump like the blood pump P1 is provided on the replacement fluid passage 5.

The replacement fluid passage 5 may alternatively be connected to the vein-side passage 12 according to a judgment made by a doctor in charge.

As shown in FIG. 1, the dialysis solution circuit 4 is provided with first and second dialysis solution chambers 21 and 22 each of which the dialysis solution is supplied to or discharged from, and which are identical in shape to each other, a solution feed passage 23 through which the fresh dialysis solution is fed to the first or second dialysis solution chamber 21 or 22, a dialysis solution supply passage 24 through which the fresh dialysis solution is supplied from the first or second dialysis solution chamber 21 or 22 to the dialyzer 2, a dialysis solution recovery passage 25 through which the used dialysis solution having passed through the dialyzer 2 is recovered into the first or second dialysis solution chamber 21 or 22, and a drain passage 26 through which the used dialysis solution is discharged from the first or second dialysis solution chamber 21 or 22 to a drain tank (not shown).

Each of the interiors of the first and second dialysis solution chambers 21 and 22 is partitioned by two diaphragms, thereby forming supply sections 21a and 22a which contain the fresh dialysis solution, recovery sections 21b and 22b which contain the used dialysis solution, and intermediate sections 21c and 22c which are formed between the supply sections 21a and 22a and the recovery sections 21b and 22b, and which are filled with silicone oil.

A silicone oil pump P3 is provided between the intermediate section 21c in the first dialysis solution chamber 21 and the intermediate section 22c in the second dialysis solution chamber 22. The volumes of silicone oil filling the intermediate sections 21c and 22c are changed by the silicone oil pump p3.

A solution feed pump (not shown) which feeds the fresh dialysis solution is provided on the solution feed passage 23. A downstream portion of the solution feed passage 23 diverges into branches extending in two directions to connect respectively to the supply sections 21a and 22a of the first and second dialysis solution chambers 21 and 22. Solution feed valves V1 and V2 are respectively provided in the branches.

An upstream portion of the dialysis solution supply passage 24 diverges into branches extending in two directions to connect respectively to the supply sections 21a and 22a of the first and second dialysis solution chambers 21 and 22. A coupler 24a to be connected to the dialyzer 2 is provided on a downstream end of the dialysis solution supply passage 24. Supply valves V3 and V4 are respectively provided in the branches.

A coupler 25a to be connected to the dialyzer 2 is provided on an upstream end of the dialysis solution recovery passage 25. A downstream portion of the dialysis solution recovery passage 25 diverges into branches extending in two directions to connect respectively to the recovery sections 21b and 22b of the first and second dialysis solution chambers 21 and 22.

A dialysis solution pump P4 for feeding the dialysis solution is provided on the dialysis solution recovery passage 25 upstream of the branches, and recovery valves V5 and V6 are provided in the branches.

An upstream portion of the drain passage 26 diverges into branches extending in two directions to connect respectively to the recovery sections 21b and 22b of the first and second dialysis solution chambers 21 and 22. A downstream portion of the drain passage 26 is connected to the drain tank (not shown). Drain valves V7 and V8 are respectively provided in the branches.

Flowing of the dialysis solution in the above-described dialysis solution circuit 4 will be described. The solution feed pump on the solution feed passage 23 and the dialysis solution pump P4 on the dialysis solution recovery passage 25 are operated. In this state, with respect to the first dialysis solution chamber 21, the solution feed valve V1 and the drain valve V7 are opened and the supply valve V3 and the retrieval valve 5 are closed.

The fresh dialysis solution then flows from the solution feed passage 23 into the supply section 21a of the first dialysis solution chamber 21 to deform the diaphragm and reduce the capacity of the recovery section 21b. The used dialysis solution contained in the recovery section 21b is thereby discharged to the outside through the drain passage 26.

On the other hand, with respect to the second dialysis solution chamber 22, the supply valve V4 and the recovery valve V6 are opened and the solution feed valve V2 and the drain valve V8 are closed. The used dialysis solution then flows into the recovery section 22b to deform the diaphragm and reduce the capacity of the supply section 22a. The fresh dialysis solution contained in the supply section 22a is thereby flowed through the dialysis solution supply passage 24 to be supplied to the dialyzer 2.

Thereafter, the solution feed valves V1 and V2, the supply valves V3 and V4, the recovery valves V5 and V6 and the drain valves V7 and V8 are alternately opened and closed to supply the fresh dialysis solution from the first or second dialysis solution chamber 21 or 22 to the dialyzer 2 through the dialysis solution supply passage 24 to recover the used dialysis solution having passed through the dialyzer 2 to the first or second dialysis solution chamber 21 or 22 through the dialysis solution recovery passage 25, thereby maintaining flowing of the dialysis solution.

If the silicone oil pump P3 is operated during dialysis treatment, for example, to feed the silicone oil in the intermediate section 21*c* of the first dialysis solution chamber 21 to the intermediate section 22*c* of the second dialysis solution chamber 22, the capacity of the intermediate section 21*c* is reduced.

A negative pressure is then produced in the recovery section 21*b* to produce a difference in pressure between the blood passage and the dialysis solution passage in the dialyzer 2, thereby enabling removal of water from blood.

A first bypass passage 27 is formed between the solution feed passage 23 and the dialysis solution supply passage 24 upstream of the branched of the solution feed passage 23. A first on-off valve V11 is provided in the first bypass passage 27.

A concentration measurement device 28 for measuring the concentration of the dialysis solution, first and second dialysis solution filters F1 and F2 for removing hazardous substance in the dialysis solution and a second on-off valve V12 are provided on the dialysis liquid supply passage 24 downstream of the branched. A downstream end of the first bypass passage 27 is connected between the branched and the concentration measurement device 28.

Each of the first and second dialysis solution filters F1 and F2 is partitioned into an upstream section and a downstream section by a semipermeable membrane. When the dialysis solution permeates through the semipermeable membrane from the upstream section into the downstream section, the semipermeable membrane removes hazardous substance.

A second bypass passage 29 for communication between the dialysis solution supply passage 24 and the dialysis solution recovery passage 25 is connected to the upstream section of the first dialysis solution filter F1. A third on-off valve V13 is provided in the second bypass passage 29.

A third bypass passage 30 for bypassing between the upstream side and the downstream side of the second on-off valve V12 is connected to the dialysis solution supply passage 24. In the third bypass passage 30 are provided in order from the upstream side a fourth on-off valve V14, the replacement fluid port 31 connected to the replacement fluid passage 5 and a fifth on-off valve V15.

The replacement fluid port 31, described below in detail, is a port to which the replacement fluid passage 5 is connected at the time of dialysis treatment to supply the dialysis solution to the replacement fluid passage 5. When preparations for dialysis treatment are made, the replacement fluid passage 5 is not connected; the dialysis solution is flowed through the third bypass passage 30 without being supplied into the replacement fluid passage 5.

In the dialysis solution recovery passage 25 are provided in order from the dialyzer 2 side a sixth on-off valve V16, a pressure sensor 32 for measuring pressure, the dialysis solution pump P4 for feeding the dialysis solution and an air removal bath 33 for removing air in the dialysis solution. A downstream end of the second bypass passage 29 is connected at a position adjacent to the upstream side of the pressure sensor 32.

A fourth bypass passage 34 for communication between the dialysis solution recovery passage 25 and the drain passage 26 is provided on the air removal bath 33, and a seventh on-off valve V17 is provided in the fourth bypass passage 34.

The air removal bath 33 has a hermetically sealed interior portion. The dialysis solution overflowing from the air removal bath 33 can be flowed into the fourth bypass passage 34 by opening the seventh on-off valve 17 in a state where the air removal bath 33 is filled with the dialysis solution.

Figure 2:
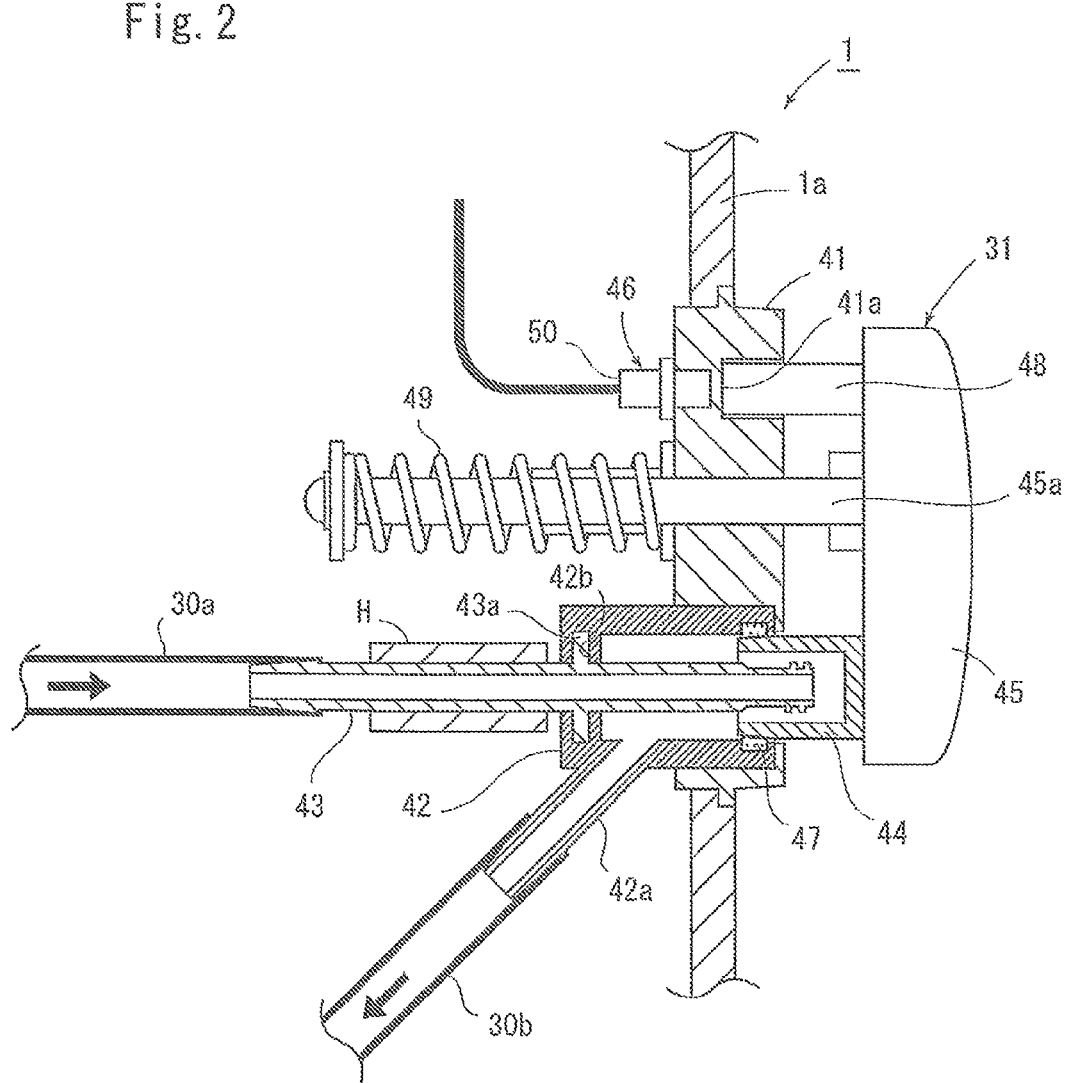
FIG. 2 is a sectional view of a replacement fluid port.

The replacement fluid port 31 provided in the third bypass passage 30 will be described with reference to FIG. 2. Referring to FIG. 2, the replacement fluid port 31 is in a state of being closed with a lid member 44 described below, with the replacement fluid passage 5 not connected to thereto.

The replacement fluid port 31 has a base member 41 fixed on a housing 1*a* of the hemodialysis apparatus 1, an outer port 42 provided in the form of a cylinder with a closed bottom and fixed to the base member 41, a cylindrical inner port 43 provided in the outer port 42 so as to extend through the bottom portion of the outer port 42, the lid member 44 which closes the inner port 43 as well as the outer port 42, a lever 45 for moving the lid member 44, and opening/closing detection means 46 for detecting an open/closed state of the lid member 44.

The base member 41 is a member generally in the form of a disk. The lever 45 is provided so as to be rotatable on a through hole formed approximately at a center of the base member 41.

The outer port 42 is made of a resin having heat resistance and is fixed so that its bottom surface faces in a lateral direction and its opening is located at an end surface of the base member 41. A ring seal 47 into which the lid member 44 is fitted is provided in a distal end portion of an inner circumferential surface of the outer port 42.

A discharge outlet 42*a* to which downstream piping 30*b* as discharge-side piping constituting the third bypass passage 30 is connected is formed in a lower portion of an outer circumferential surface of the outer port 42.

The inner port 43 is a tubular member made of a metal and provided coaxially with the outer port 42. The inner port 43 is passed through a bottom surface of the outer port 42. Upstream piping 30*a* as supply-side piping constituting the third bypass passage 30 is connected to a base portion of the inner port 43.

A flange 43*a* is formed approximately at a center of the inner port 43 and held by being fitted into a recessed portion 42*b* formed along the bottom surface of the outer port 42 so as not to move relative to the same.

A heater H for heating the inner port 43 is provided on an outer circumferential surface of the inner port 43 between the upstream piping 30*a* and the outer port 42.

A rubber heater H, a band heater H or a nickel-chrome wire for example may be used as the heater H. The temperature of the heater can be controlled by the control means. The temperature of the heated inner port 43 can be measured with a temperature sensor (not shown).

A distal end of the inner port 43 projects out of an opening of the outer port 42 to the outside of a main body 7. A helical groove for connection of the replacement fluid passage 5 is formed in an outer circumferential surface of the inner port 43 at the distal end.

The lid member 44 has the shape of a bottomed cylinder. In a closed state illustrated in FIG. 2, an outer circumferential surface of the lid member 44 is maintained in close contact with the ring seal 47 provided in the inner circumferential surface of the outer port 42, thereby forming a space in the outer port 42 and the lid member 44.

In this closed state, a space is formed between the inner port 43 and the lid member 44, thereby enabling the dialysis solution discharged from the inner port 43 to flow through the space formed by the lid member 44 and the outer port 42 to be discharged out of the discharge outlet 42*a*.

That is, in the replacement fluid port 31 in the state of being closed with the lid member 44, the dialysis solution having flowed into the upstream piping 30a of the third bypass passage 30 passes through the space formed by the lid member 44 and the outer port 42 and is discharged through the downstream piping 30b.

Conversely, when the replacement fluid passage 5 is connected to the inner port 43 in the open state after removing the lid member 44 from the outer port 42, the opening portion of the outer port 42 is exposed to the outside and the dialysis solution flows from the inner port 43 into the replacement fluid passage 5 and flows into the artery-side passage 11 of the blood circuit 3.

The lever 45 is pivotally supported by a rod 45a provided approximately at a center so as to be rotatable relative to the base member 41. The lid member 44 is fixed on the lever 45 at one end of the same, and a pin 48 is provided on an end portion of the lever 45 at the opposite end toward the main body 7.

The rod 45a is passed through the base member 41. A spring 49 is resiliently interposed between a portion of the rod 45a projecting inwardly in the main body 7 and the base member 41. The lever 45 is constantly urged in a direction toward the base member 41 by the spring 49.

Bottomed stopper holes 41a adapted to receive the pin 48 and stop the lever 45 from rotating are formed in two places in the base member 41. The pin 48 is received in one of the stopper holes 41a when the lever 45 is positioned in the closed state shown in FIG. 2.

The other stopper hole (not shown) is formed at a position at which the lever 45 is held at such an angle as not to hinder attachment of the replacement fluid passage 5.

The opening/closing detection means 46 is constituted by a magnet (not shown) provided on the distal end of the pin 48, and a magnetism sensor 50 attached to the base member 41 on the reverse side opposite from the stopper hole 41a.

In the closed state illustrated in FIG. 2, the pin 48 is inserted in the stopper hole 41a, the magnet is close to the magnetism sensor 50, and the state in which the replacement fluid port 31 is closed is recognized by detecting the magnetic force of the magnet with the magnetism sensor 50.

When the lever 45 is turned from the state shown in FIG. 2, the pin 48 is detached from the stopper hole 41a and the magnetic force of the magnet cannot be detected with the magnetism sensor 50. As a result, the state in which the replacement fluid port 31 is open is recognized.

The control means is set to be incapable of heating the inner port 43 with the heater H when the replacement fluid port 31 is opened.

A method of operating the hemodialysis apparatus 1 having the above-described construction will be described. After the completion of the preceding dialysis treatment, the dialyzer 2 and the blood circuit 3 are detached from the hemodialysis apparatus 1, and the dialysis solution supply passage 24 and the dialysis solution recovery passage 25 are directly connected to each other by the couplers 24a and 25a.

Since the replacement fluid passage 5 branches off from the blood circuit 3, the replacement fluid passage 5 is detached from the replacement fluid port 31, and the replacement fluid port 31 is closed with the lid member 44.

In this state, the interior of the dialysis solution circuit 4 is sterilized by flowing a cleaning liquid or hot water therethrough. The interior of the dialysis solution circuit 4 is filled with the cleaning liquid supplied from the solution feed passage 23 by operating the first and second dialysis solution chambers 21 and 22 and the on-off valves as described above.

More specifically, the cleaning liquid supplied from the first or second dialysis solution chamber 21 or 22 flows through the dialysis solution supply passage 24, passes through the couplers 24a and 25a, and thereafter flows through the dialysis solution recovery passage 25. The used dialysis solution contained in these passages is replaced with the cleaning liquid.

Simultaneously, the first to seventh on-off valves V11 to V17 provided in the dialysis solution circuit 4 are operated as desired to also replace the dialysis solution contained in the first to fourth bypass passages 27, 29, 30, and 34 with the cleaning liquid.

After the cleaning liquid is flowed through the dialysis solution circuit 4 in the above-described way for a predetermined time period, the feed of the cleaning liquid from the first and second dialysis chambers 21 and 22 is stopped to leave the cleaning liquid in the dialysis solution circuit 4.

When the cleaning liquid is flowed through the dialysis solution circuit 4, the replacement fluid port 31 provided in the third bypass passage 30 is closed and the outer port 42 is closed with the lid member 44. Therefore, the cleaning liquid discharged from the inner port 43 fills the space formed by the outer port 42 and the lid member 44.

In the state where the dialysis solution is staying in the space after stopping the feed of the cleaning liquid from the first and second dialysis solution chambers 21 and 22, the heater H provided on the inner port 42 is operated.

The inner port 42 is then heated to sterilize the portion to which the replacement fluid passage 5 is connected. Further, the outer circumferential surface of the inner port 42 exposed in the space can also be sterilized with the cleaning liquid heated by the conduction of heat. The cleaning liquid heated by the conduction of heat also contributes to heat sterilization.

In this embodiment, the replacement fluid port 31 can be reliably sterilized by heating the inner port 42, for example, to 80 to 100° C. with the heater H.

After the completion of sterilization of the replacement fluid port 31 in the above-described way, an operation to replace the cleaning liquid with the fresh dialysis solution is performed by flowing the fresh dialysis solution through the dialysis solution circuit 4.

When the replacement with the fresh dialysis solution in the replacement fluid circuit 4 is completed, the control means produces a display on a monitor or the like (not shown) informing that the dialyzer 2 and the blood circuit 4 can be connected. The operator then changes the replacement fluid port 31 from the closed state to the open state and connects the replacement fluid passage 5.

In the above-described embodiment, the inner port 43 is heated with the heater H in a state where the replacement fluid port 31 is closed with the lid member 44 and where the space formed by the outer port 42 and the lid member 44 is filled with the cleaning liquid, thus enabling the portion of the inner port 43 exposed to the outside to be subjected to a high level of sterilization.

In the hemodialysis apparatus 1 in the present embodiment in particular, there is a need to perform a high level of sterilization on the replacement fluid port 31 since the replacement fluid passage 5 for supplying the dialysis solution to a patient through the blood circuit 3 is connected to the replacement fluid port 31 for the purpose of performing on-line HDF, and the high level of sterilization can be performed with the above-described heater H.

In the dialysis solution circuit 4 in the above-described embodiment, the intermediate sections 21c and 22c are formed in the first and second dialysis solution chambers 21 and 22 and removal of water is performed by reducing the capacity of the intermediate section 21*c* or 22*c* during dialysis treatment. However, the arrangement may alternatively be such that the intermediate sections 21*c* and 22*c* are removed; a bypass passage provided with a water removal pump is provided between the dialysis solution recovery passage 25 and the drain passage 26; and removal of water is performed with the water removal pump.

REFERENCE SIGNS LIST

1 Hemodialysis apparatus
2 Dialyzer
3 Blood circuit
4 Dialysis solution circuit
5 Replacement fluid passage
31 Replacement fluid port
42 Outer port
43 Inner port
44 Lid member
H Heater

The invention claimed is:

1. A connection port in a dialysis apparatus comprising:
a cylindrical outer port to which liquid discharge-side piping is connected; an inner port to which liquid supply-side piping is connected, and which is provided in the outer port; and a lid member which closes the outer port, a liquid from the inner port being flowed through a space formed by the lid member and the outer port and discharged from the outer port when the lid member is in a closed state, the inner port being exposed to the outside when the lid member is in an open state, enabling a liquid passage to be connected to the inner port,
wherein the outer port is in the form of a cylinder with a closed bottom and is provided with an opening which is closed by the lid member which has the shape of a cylinder with a closed bottom,
the inner port has an end portion which projects outside the opening of the outer port and is fixed to the outer port so as to penetrate the closed bottom of the outer port from the outside to the inside, and further a heater is provided for a portion of the inner port projecting outside the outer port, and
when the lid member is in the closed state, the inner port is heated with the heater to sterilize the portion of the inner port exposed to the outside.

2. A dialysis apparatus having the connection port according to claim 1, the apparatus comprising:
a dialyzer for performing hemodialysis; a blood circuit for flowing blood through the dialyzer; and a dialysis solution circuit for flowing a dialysis solution through the dialyzer, the apparatus comprising:
a replacement fluid passage branching off from the blood circuit; and
the connection port that is provided in the dialysis solution circuit, to which connection port the replacement fluid passage can be connected,
wherein the inner port is heated with the heater to sterilize a portion of the inner port connected to the replacement fluid passage.

3. The connection port in a dialysis apparatus according to claim 1, wherein the outer port is made of a heat-resistant resin and
a flange is formed on the portion of the inner port extending through the outer port, and a recessed portion into which the flange is fitted is formed in the bottom of the outer port.

* * * * *